June 15, 1965 O. HONDA Plant Pat. 2,535
CARNATION
Filed Nov. 6, 1963
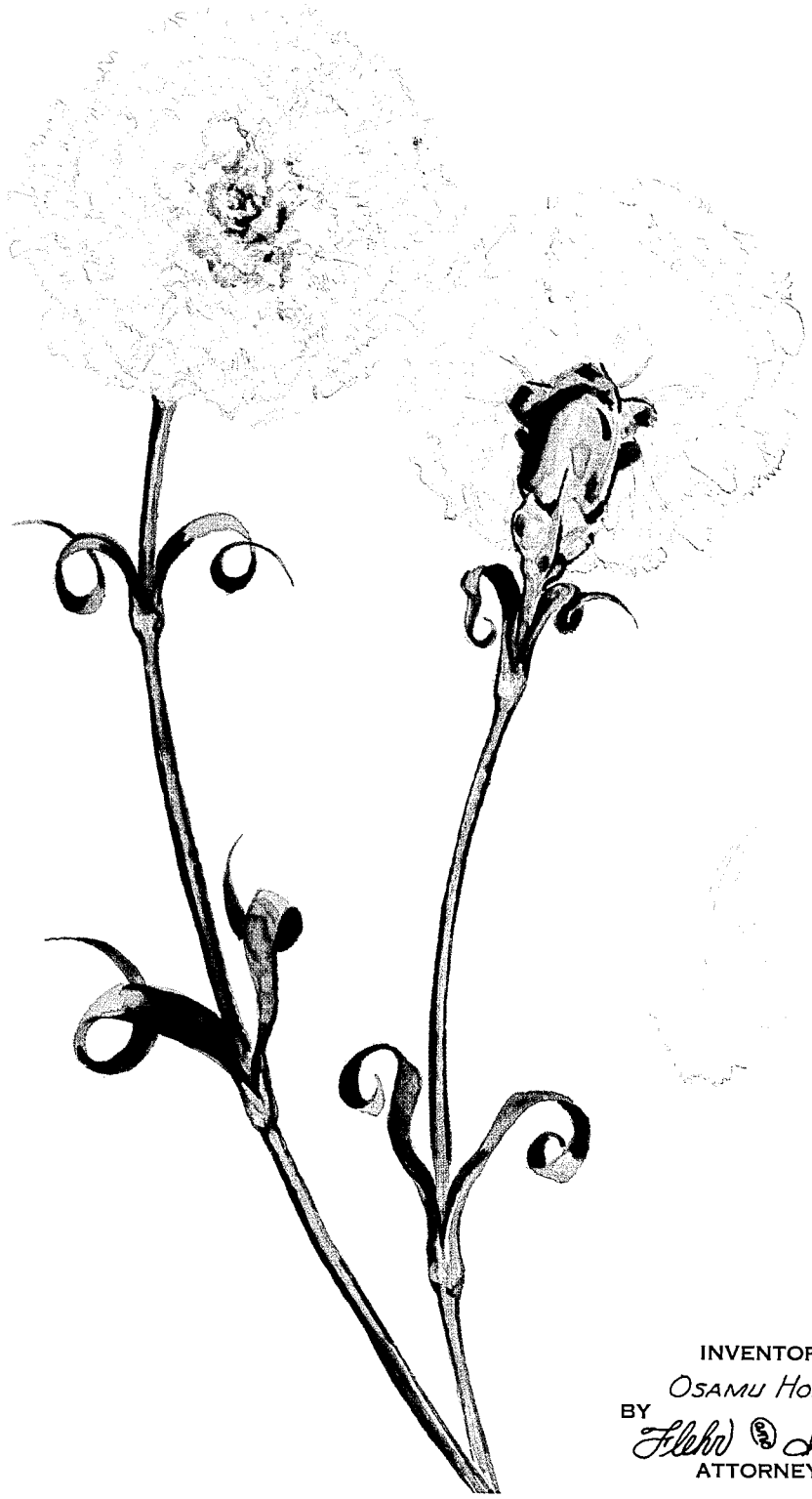
INVENTOR
OSAMU HONDA
BY
Flehr & Swain
ATTORNEY United States Patent Office Plant Pat. 2,535
Patented June 15, 1965

2,535
CARNATION

Osamu Honda, Redwood City, Calif., assignor to Woodside Nurseries Co., Redwood City, Calif., a corporation of California Filed Nov. 6, 1963, Ser. No. 321,988
1 Claim. (Cl. Plt.—70)

This invention relates to a carnation and more particularly to a carnation which has a flower having unique color characteristics.

This new carnation is from an unnamed sport which had a color of light salmon pink with magenta pink stripes and which has not been registered. The parentage of this unnamed sport is Peterson's New Light Pink (unpatented) registered with the American Carnation Society of New Augusta, Indiana on February 2, 1960, by S. Arthur Peterson, Inc., Lexington, Massachusetts. Peterson's New Light Pink having a color of light salmon pink is a sport of Mamie (unpatented) registered with the American Carnation Society on February 5, 1951, by E. C. Geiger, North Wales, Pennsylvania and has a color of white with red variegations. Mamie is a sport of the carnation shown in United States Letters Plant Patent No. 669, issued January 15, 1946, to William Sim.

Since the color break was first observed many hundreds of cuttings have been planted.

Asexual propagation of the newly discovered carnation was made at Redwood City, California by taking cuttings in the years 1961, 1962 and 1963 and growing them. The cuttings so taken and grown have consistently produced flowers or blossoms having the new and distinctive colors hereinafter described more in detail.

In the drawing there are illustrated specimens of this new variety of carnation, showing the flower in full bloom.

The following is a detailed description of the new carnation.

The description of the carnation in United States Letters Patent No. 669 is applicable to the newly discovered variety with one exception, namely: the color of the flower.

The petals of the flower are flaked throughout with slightly darker markings while the bases of the petals are very light pink or white in color. The reverse side of the petals are similarly flaked. The overall view at a slight distance is very pleasing to the human eye. The color of the petal field closely approximates the color shown in Plate 13. Swatches A–3 and A–4 of the Reinhold Color Atlas published by the Reinhold Publishing Corporation, New York, New York (Library of Congress Catalog No. 62–8756). The petal field is heavily flaked with colors closely approximating the colors shown in Swatches B–6 and B–7 of the same color atlas. The closest descriptive term for the color of the flower is Persian Rose identified as 13B8 in the above named color atlas.

I claim:

The new and distinct variety of carnation substantially as herein described and illustrated.

No references cited.

ABRAHAM G. STONE, *Primary Examiner.*